United States Patent
Christensen (10) Patent No.: US 6,224,580 B1
(45) Date of Patent: May 1, 2001

(54) APPARATUS FOR TREATMENT OF THE FEMALE PELVIC FLOOR

(76) Inventor: Jane N. Christensen, Sdr. Boulevard 14, DK-5000 Odense C (DK)

( * ) Notice: Subject to any disclaimer, the term of this patent is extended or adjusted under 35 U.S.C. 154(b) by 0 days.

(21) Appl. No.: 09/381,726

(22) PCT Filed: Mar. 26, 1998

(86) PCT No.: PCT/DK98/00127
§ 371 Date: Oct. 20, 1999
§ 102(e) Date: Oct. 20, 1999

(87) PCT Pub. No.: WO98/42400
PCT Pub. Date: Oct. 1, 1998

(30) Foreign Application Priority Data

Mar. 26, 1997 (DK) .................................................. 0356/97

(51) Int. Cl.[7] .................................................. A61M 31/00
(52) U.S. Cl. .................................................. 604/275
(58) Field of Search .............. 604/96, 101; 606/191–194

(56) References Cited

U.S. PATENT DOCUMENTS

| 899,477 | * | 9/1908 | Williams | 606/193 |
|---|---|---|---|---|
| 923,303 | * | 6/1909 | Shults | 606/193 |
| 2,026,747 | * | 1/1936 | Nemzek | 606/193 |
| 3,799,170 | * | 3/1974 | Walsh et al. | 606/193 |
| 4,198,981 | * | 4/1980 | Sinnreich | 606/193 |
| 4,664,114 | * | 5/1987 | Ghodsoan | 606/193 |
| 5,338,297 | * | 8/1994 | Kocur et al. | 604/96 |

FOREIGN PATENT DOCUMENTS

| 3803727 | 4/1989 | (DE) . |
|---|---|---|
| 3800744 | 5/1989 | (DE) . |
| 2297036 | 7/1996 | (GB) . |
| 2071285 | 1/1997 | (RU) . |

* cited by examiner

*Primary Examiner*—Manuel Mendez
(74) *Attorney, Agent, or Firm*—Dykema Gossett PLLC (57) ABSTRACT

An apparatus, in particular for use in the antenatal period of pregnant women for insertion into the vagina, the main function of which is to dilate muscular, tendinous and connective tissue in the pelvic floor so as to make these tissue structures more flexible, includes a length of hose (4) mounted on a mandrel (3) and is expandable by means of a fluid, the length of hose being connectable with the fluid through at least one channel (6) in the mandrel. The mandrel is formed with at least one channel which extends longitudinally through it and terminates outside the user in the use of the apparatus. The mandrel with the length of hose may be provided with a replaceable cover which adds to the hygiene and safety.

15 Claims, 7 Drawing Sheets

APPARATUS FOR TREATMENT OF THE FEMALE PELVIC FLOOR

BACKGROUND OF THE INVENTION

1. Field of the Invention

The present invention relates to an apparatus, particularly for use by pregnant women, which includes a mandrel for insertion into the vagina, the main function of the apparatus being to dilate muscular, tendinous and connective tissue in the pelvic floor (diaphragma pelvis) and the perineum so as to make these tissue structures more elastic with the purpose of reducing the frequency and the size of traumatic injuries during the actual childbirth, such as breaks and ruptures, and of reducing the number of surgical interventions (episiotomy). A secondary function is that the apparatus may moreover be used for retraining a flabby pelvic floor musculature, e.g., caused by childbirth, or for ordinary maintenance training, and may thus also contribute to contraction of the above-mentioned structures.

2. The Prior Art

A single apparatus of this type is known, viz. from EP 0 574 966 B1. This apparatus, which has a purely mechanical action, includes a distendible mandrel for insertion into the vagina. The mandrel includes a plurality of elements which may be displaced radially from each other by means of a wedge effect or linkage in order to expand the pelvic floor. The apparatus has a relatively heavy and clumsy appearance, but provides excellent control when training expansion of the pelvic floor, e.g., for an imminent birth. The apparatus can give a measure of the expansion of the pelvic floor from time to time and protects against an unintentional too rapid expansion that may cause damage to the pelvic floor, as the user herself controls the expansion. The excellencies of the apparatus, however, are overshadowed by the circumstance that the apparatus is not very handy and convenient in use. Thus, the apparatus has the undesirable property that, when operated, it can rotate in the vagina.

The object of the invention is to provide an apparatus of the above-mentioned type which is easier to use than the purely mechanically acting apparatus mentioned above.

SUMMARY OF THE INVENTION

This object is achieved according to the invention by an apparatus which is characterized in that the mandrel has mounted thereon an expandable length of hose which may be connected with an air pump or the like for the fluid through at least one channel in the mandrel, and that the mandrel has a vent channel extending longitudinally through it and terminating outside the user in use. The use of a length of hose provides for an expansion in the transverse direction alone, while allowing a vent channel to be provided. Insertion of this apparatus into the vagina is easier than the purely mechanical one, as the apparatus according to the invention may basically be made smaller, i.e., primarily thinner. Furthermore, the apparatus does not tend to rotate in operation and use.

It will be appreciated that the apparatus according to the invention differs from the type of devices comprising a balloon, which are exclusively used for measuring the muscular strength of the pelvic floor and retraining it, cf. e.g., U.S. Pat. No. 4,050,499 which discusses Kegel's Perineometer among other things. The apparatus also differs from dilators as described in DE 38 03 727 C1 in which a mandrel is coated by a closed envelope which leaves no possibility of an evacuation channel.

The invention also relates to a protective cover for the apparatus according to the invention. The cover is formed by a length of hose intended to be applied to mandrels and at least secured at or near one end. The protective cover, which is discarded after each use of the apparatus, serves a hygienic purpose as well as a safety purpose in the event that the dilated length of hose should break.

The use of a liquid as the fluid readily provides a measure for the expansion like in the mechanical apparatus. The situation is different when using a gas, typically atmospheric air, as the fluid since this is compressible. To prevent expansion altogether beyond the permissible amount, a restrictive envelope, e.g., in the form of a net, may be inserted over the length of hose, which net may optionally be integrated in the length of hose. Alternatively, the cover may be shaped so as to have a restrictive effect, and graduation of the maximum size allowed for the covers and coding, e.g., by colour, may provide a measure of the expansion achieved for each use. This may be combined with an adjustable pressure relief valve in the apparatus which sets an upper limit to how hard the length of hose may be inflated.

For the secondary function of the apparatus, i.e., retraining of a flabby pelvic floor musculature, the mandrel may be provided with a casing which is applied over the front of the mandrel and which protrudes somewhat across the expandable length of hose, so that said length is active only on the rearmost part, i.e., precisely the part with which the pelvic floor musculature is retrained.

The invention will be described more fully below with reference to the example illustrated in the accompanying drawing. In the drawings:

DETAILED DESCRIPTION OF THE PREFERRED EMBODIMENTS

Figure 1:
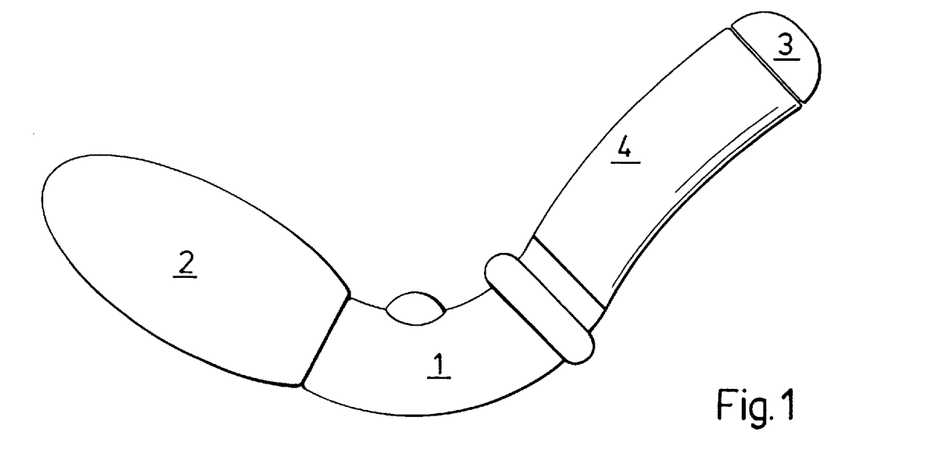
FIG. 1 shows an embodiment of the apparatus according to the invention, seen from the side.

The apparatus shown in FIG. 1 comprises an intermediate member 1 whose rear end is connected with an air pump 2 in the form of a rubber ball, and which forwardly merges into a mandrel 3 around which a length of hose 4 is secured, said length being inflatable by means of the hand pump.

Figure 2:
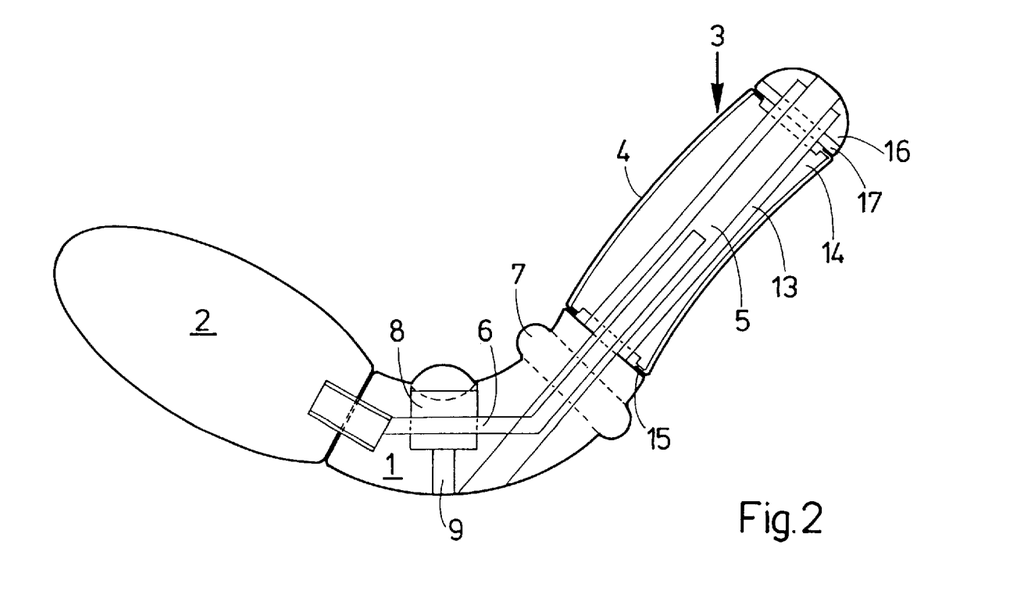
FIG. 2 shows a longitudinal section of the apparatus of FIG. 1.

As will appear from FIG. 2, a through-going pressure equalization channel is provided in the mandrel 3 and the intermediate member 1, said channel extending from the tip of the mandrel and out on the underside of the intermediate member. The intermediate member has an air channel 6 which connects the air pump 2 with the inner side of the length of hose 4 via a duct in the mandrel shown in dashed line and having distribution channels (not shown) which terminate on the upper side of the mandrel.

The shape of the mandrel is adapted to the vagina, and the apparatus as a whole is shaped for easy insertion into it. The intermediate member has a ring-shaped expansion 7 which indicates the maximum insertion of the mandrel into the vagina. During insertion, air in the abdomen will be evacuated through the air equalization channel 5. When the apparatus is in position, the length of hose 4 is inflated to the desired firmness. If the length of hose breaks by accident, the air escaping into the abdomen will likewise be evacuated through the pressure equalization channel 5.

After completed use the apparatus may be vented by deflating the length of hose by means of a valve 8 in the air channel 6 of the intermediate member which communicates with a branch 9 to the underside of the intermediate member. A manometer may be connected with the branch, allowing a picture of the muscular strength in the area to be obtained by the pressure.

Figure 3:
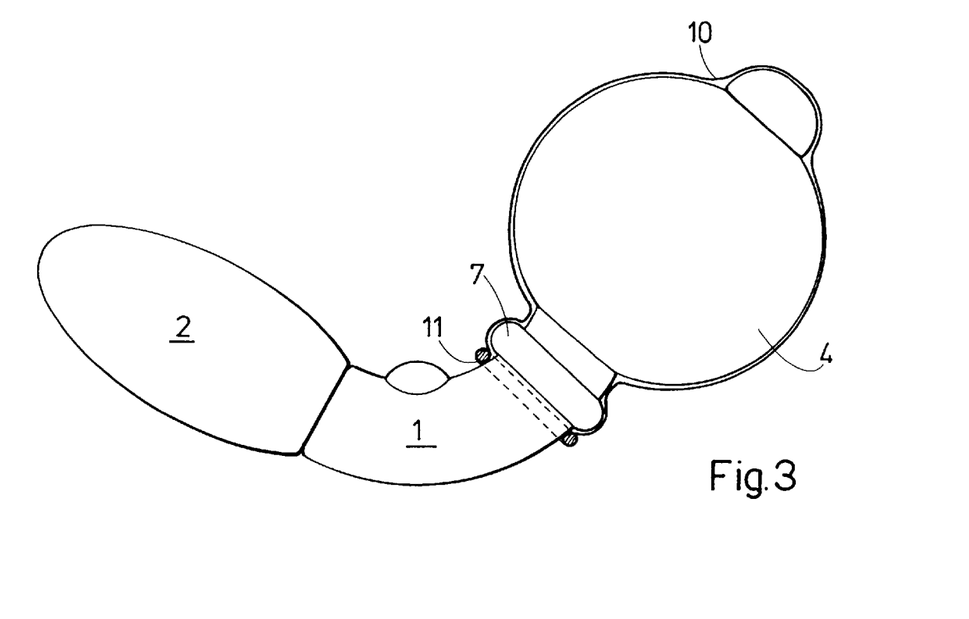
FIG. 3 shows the apparatus of FIG. 1 in a dilated state and provided with a protective cover.

For reasons of hygiene and safety, the mandrel may be provided with a replaceable cover 10 in the form of a length of hose prior to each exercise, see FIG. 3 which shows the apparatus in its state of maximum dilation. One end of the cover 10 is passed into the pressure equalization channel 5, and its other end is rolled down over the mandrel. To facilitate the application, the end of the cover intended to he inserted into the channel 5 may be given a tubular shape or be provided as a decided tube which fits here. The application of the cover is carried out before the apparatus is inflated. An elastic ring 11 is arranged at the outer end of the cover, and this ring is moved across the elevation 7 and down in front of it. There is still a passageway through the pressure equalization channel 5 for pressure equalization during insertion and for discharge of the air in the event that the length of hose 4 should become leaky. In that respect the cover has the additional advantage that it prevents the air from penetrating into the abdomen, but conveys it either directly into the air channel or allows the air to escape below the cover 10 at the attachment 11 to the intermediate member.

Apart from the aspect of hygiene, the cover 10 also turns out to have a stabilizing effect on the length of hose 4. It has been found that in some cases the length of hose is not inflated uniformly around the mandrel. The phenomenon may possibly be ascribed to the circumstance that the latex is produced with a relatively great inaccuracy in thickness. The cover has been found to have an aligning effect on the inflated length of hose, i.e. it will be positioned symmetrically or essentially symmetrically with respect to the mandrel.

A latex of a thickness in the range of 0.8–1.4 mm is used for the length of hose. A thinner latex makes the length of hose too unstable, while a thicker latex is too stiff.

Figure 4:
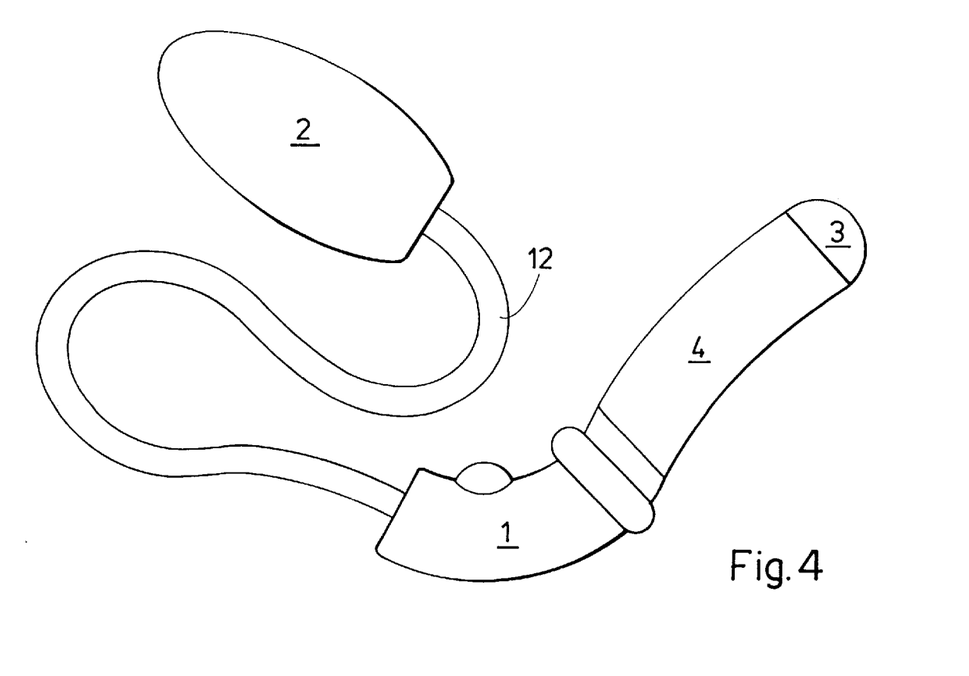
FIG. 4 shows the apparatus of FIG. 1 where the air pump is connected with the apparatus by a hose.

For the users who find it inconvenient to operate the apparatus with the air pump mounted directly on the end of the intermediate member, the air pump may be removed and connected with a hose 12 of a suitable length, as shown in FIG. 4.

The apparatus is handy and easy to operate in contrast to the previous purely mechanical solution, just as the hygiene and safety in use are great.

Referring to FIG. 2 again, it is noted that the intermediate member 1 has a polygonal, e.g. hexagonal, stem-shaped extension 13 which forms the inner part of the mandrel, while the outer part 14 is pushed inwardly thereover. The length of hose 4 is secured in that it is fixed with the ends between the part 14 and the breast 15 of the intermediate member 1 and a dome-shaped nut 16 which is screwed on to a threaded member that terminates the hexagonal stem. A washer 17 is arranged between the nut 16 and the part 14.

Figure 5:
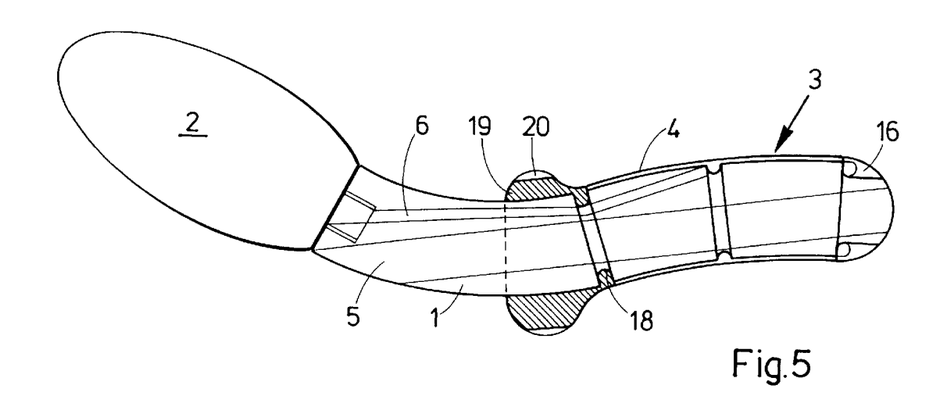
FIG. 5 shows a longitudinal section through a variation of the apparatus shown in FIGS. 1–4.

A variation of the above-mentioned embodiment is shown in FIG. 5 of the drawing in which the intermediate member 1 and the mandrel 3 are made in one piece. For attachment of the length of hose 4, an annular groove 18 is provided at the end of the mandrel toward the intermediate member to receive the end of the length of hose. For retention of it, the elevation is shaped as a detachable locking ring 19 which may be pushed inwardly over the intermediate member, and which is locked in the groove 18 by a snap lock connection. The other end of the length of hose 4 is secured by means of the nut 16, which may alternatively be provided as a ring-shaped button which may be clicked on to the end of the mandrel by a snap lock connection, said mandrel being in that case formed with the corresponding locking parts instead of threads. Instead of incorporating the vent valve in the intermediate member, an air pump 2 having an integrated vent valve may be used.

If the end of the mandrel is allowed to be uncovered, one end of the cover 10 may be secured by the nut 16, while the other end is correspondingly secured on the outer side of the locking ring 19. To facilitate the discharge of air below the elastic ring of the cover in the event that the length of hose 4 should be leaky, the locking ring 19 is provided with grooves 20.

Figure 6:
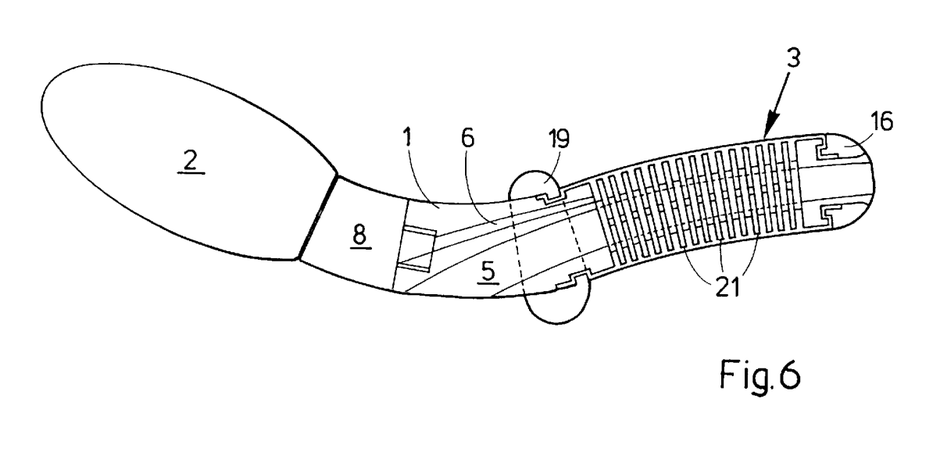
FIG. 6 shows a longitudinal section through a variation of the apparatus shown in FIG. 5.

To make the apparatus, which is made of plastics, lighter, the mandrel 3, as shown in FIG. 6, may be formed with ribs 21, thereby reducing the required amount of material. The ribs 21 are covered by the length of hose 4 so that the user will perceive the apparatus as being an essentially smooth mandrel. In contrast to the previously shown embodiments, the pressure equalization channel 5 is curved here, thereby allowing the intermediate member 1 to be made less curved than when the air channel is rectilinear. The latter requires a relatively great radius of curvature of the intermediate member for the air channel to terminate on the underside thereof. Here too, the vent channel 8 is part of the air pump, and the air channel 6 here terminates in the space to the first rib. In the embodiment shown, the locking ring 19 is composed of two halves which may be locked mutually around the apparatus by a snap lock connection. The end 16 of the mandrel is here shaped as a ring-shaped button which is snapped on to the mandrel.

Figure 7:
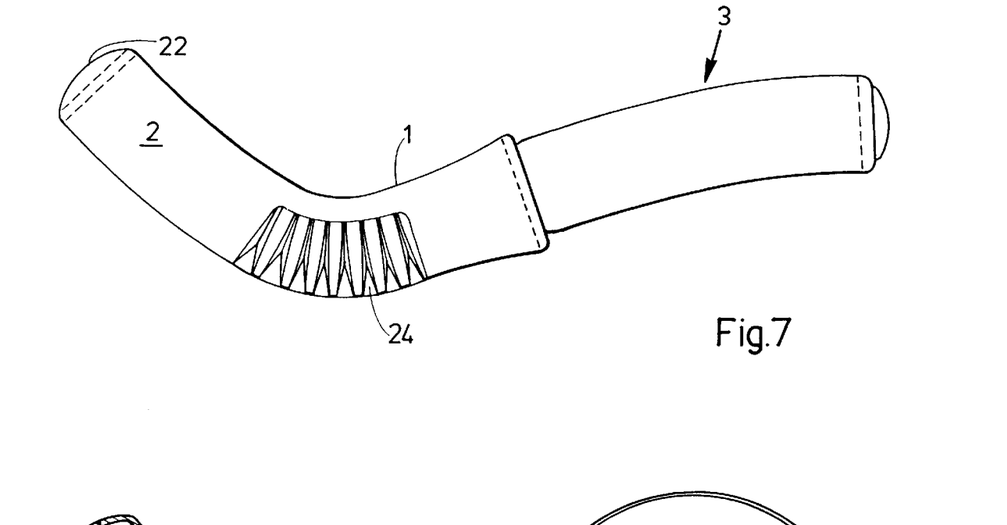
FIG. 7 shows a second embodiment of the apparatus according to the invention, seen from the side.
Figure 8:
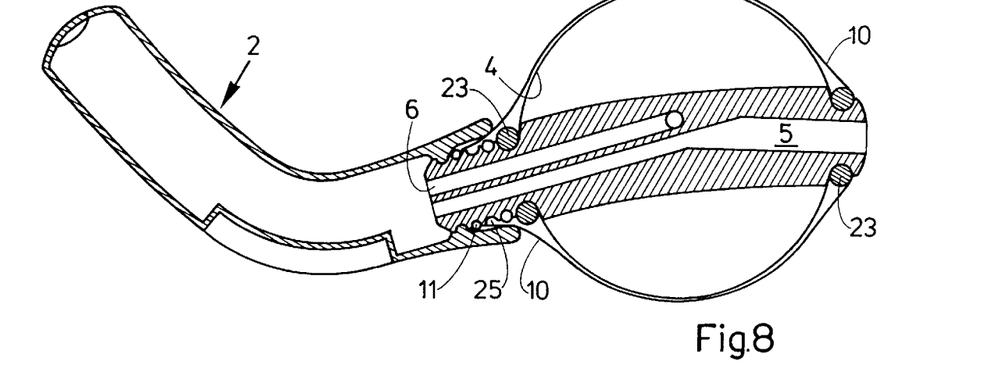
FIG. 8 shows a longitudinal section through the apparatus of FIG. 7 in an inflated state.

Still another embodiment of the apparatus of the invention is shown in FIGS. 7 and 8 of the drawing. Like before, the main components of the apparatus are an air pump 2, an intermediate member 1 and a mandrel 3. The air pump, which is not shown in detail in the drawing, is operated by a push button 22 at the end. The air pump and the intermediate member are applied as an integrated unit to the end of the mandrel by a snap lock connection. The length of hose 4 is retained with rings 23 at the ends in grooves in the mandrel. There is communication from the pump with the air channel 6 which, with transverse channels, extends out on the side of the mandrel. The central air channel 5 communicates with the outer side of the apparatus through openings 24 in the intermediate member 1. The protective cover 10 is attached at the free end of the mandrel by the ring 23 which secures the length of hose, and the other end is secured by the elastic ring 11 in a groove in the mandrel and is secured in the connection of the pump/intermediate member with the mandrel. In case of leakage in the length of hose, the air escapes through channels (not shown) which communicate with a groove 25 at the end of the mandrel. The air is discharged to the surroundings via the openings 24.

Figure 9:
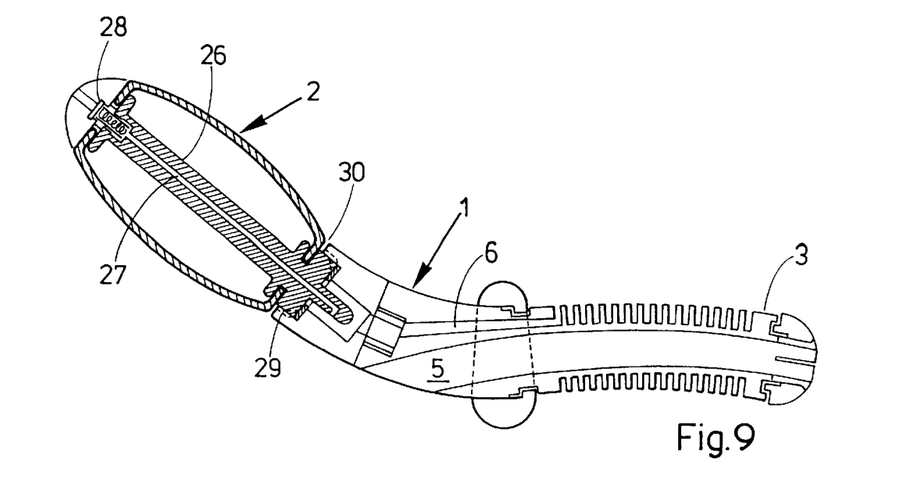
FIG. 9 shows a longitudinal section through the apparatus with an alternative embodiment of the air pump.
Figure 10:
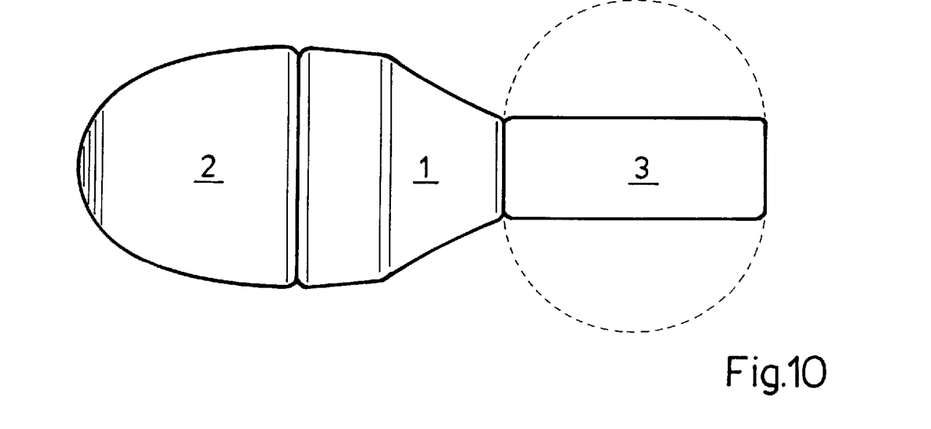
FIG. 10 shows a lateral view of a further embodiment of the apparatus according to the invention.
Figure 11:
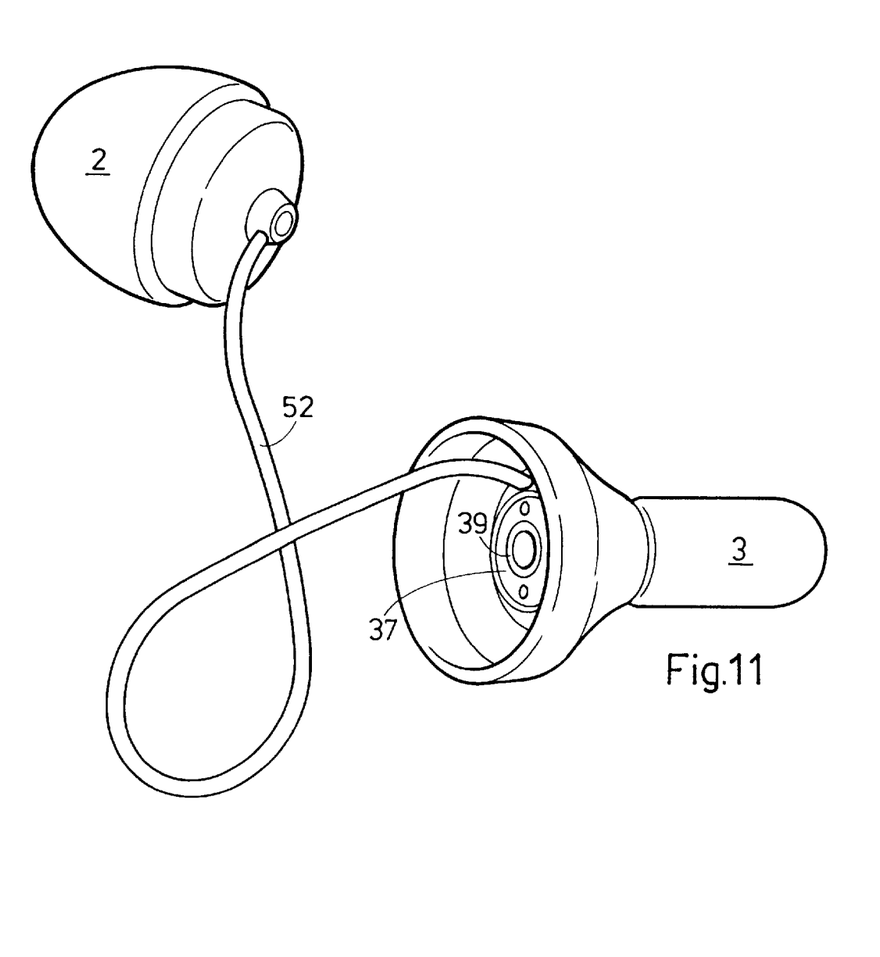
FIG. 11 shows a perspective view of the apparatus shown in a disassembled state.
Figures 12, 13:
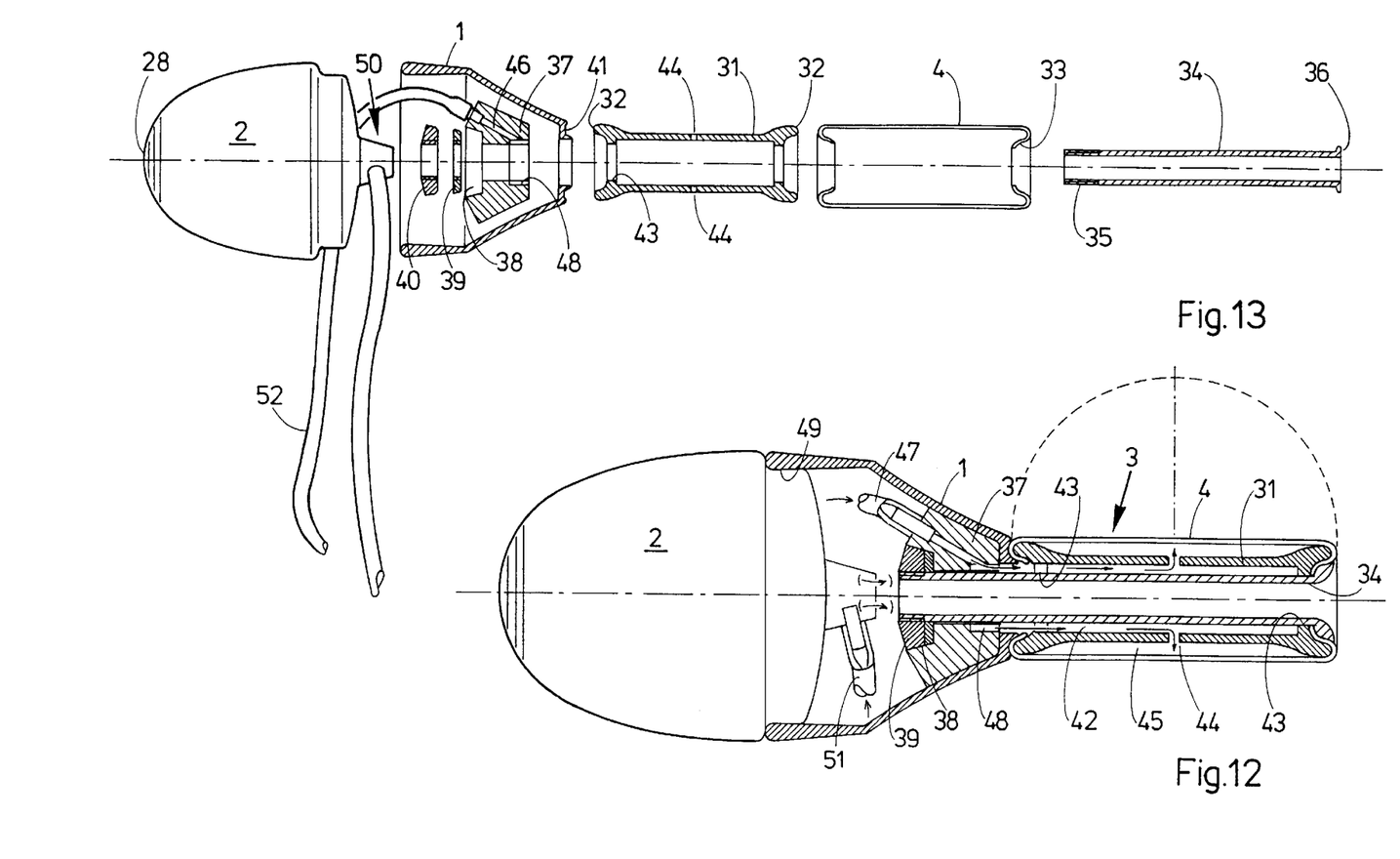
FIG. 12 shows a longitudinal section through the apparatus as shown in FIG. 10.
FIG. 13 shows an exploded view of the apparatus.
Figure 14:
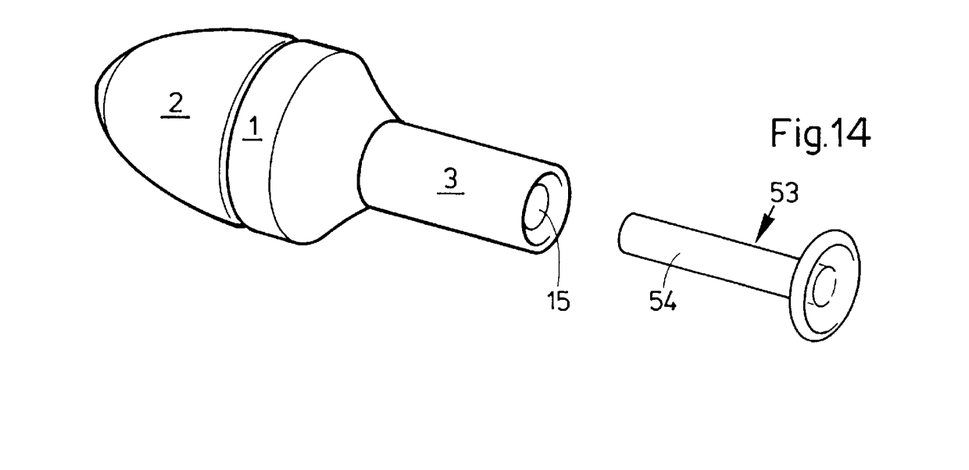
FIG. 14 shows a perspective view of the apparatus together with a cover for application to its mandrel.
Figure 15:
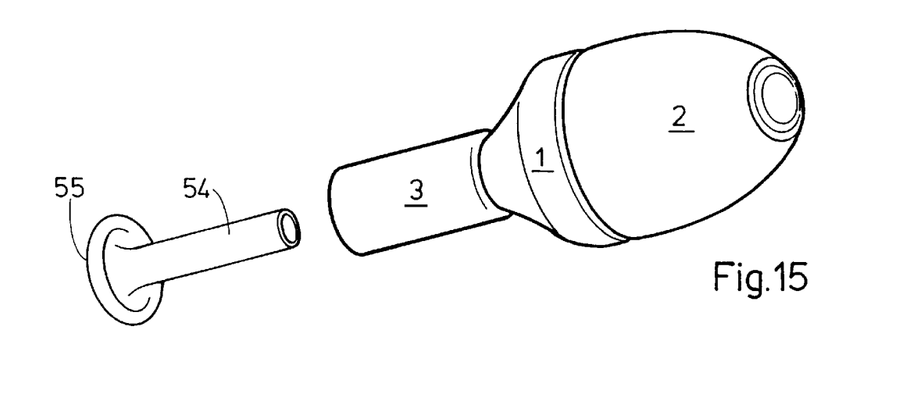
FIG. 15 shows the same as FIG. 14, but seen from the other end of the apparatus.

A special embodiment of the air pump 2 is shown in FIG. 9, said pump accommodating a rod 26 having a through channel 27 at whose free end a non-return valve 28 is arranged. The rod is connected with a valve mechanism 28 in the intermediate member 1. Inflation of the length of hose takes place by squeezing the pump ball, as described in connection with FIGS. 1–6, there being an air passage in the rod from the channel therein to the interior of the ball. Venting of the apparatus takes place by pressing the end of the rod 26 inwards toward the intermediate member 1, whereby the valve mechanism 28 opens to allow air to flow out into a gap 29 between the air ball and the intermediate member 1.

FIGS. 10–13 of the drawing show a further embodiment of the apparatus according to the invention, in which the same components are designated by the same reference numerals as in the foregoing. Here, the mandrel 4 is composed of an outer pipe 21 having a collar 23 at each end around which the length of hose 4 is secured with the ends, which are shaped so as to enter into the tubular shape of the length of hose, i.e., the ends of the length of hose are rolled over the collars of the outer pipe. The mandrel is assembled with an inner pipe 34 having a threaded portion 35 at one end and a flange 36 at the other end. During assembly, the inner pipe 34 is moved into the outer pipe 31 which has been coated with the length of hose 4 beforehand. The inner pipe is moved further on through a hole, intended for the purpose, at the end of the intermediate member 1, which is here shaped as a bowl-shaped jacket. Before the bottom of this, an insert 37 having a central hole for the inner pipe is arranged. The free end of the insert 37 is formed with a recess 38 to receive a washer 39 as well as a nut 40, which may be screwed on to the end of the inner pipe 34 for clamping the apparatus. As a result of the clamping, the outer end of the length of hose 4 is secured between the collar 32 of the outer pipe and the flange 36 of the inner pipe, while the inner end is fastened between the collar 32 of the outer pipe and the bottom of the intermediate member 1, which is here formed with a recess 41 corresponding to the collar 32.

In the assembled state, there is a ring-shaped cavity 42 between the inner and outer pipes 31, 34, as the inner pipe, at each end, has an internal flange 43 which engages the outer side of the inner pipe. Centrally on the outer pipe there are holes for the air out to the chamber below the length of hose 4.

The insert 37 has an air channel 46 therein which terminates in a hose connector 47 on the free end face of the insert and terminates in a ring-shaped recess 48 at the other end toward the mandrel, from which the air can pass on through openings in the adjoining flange 43 of the outer pipe and further on to the cavity 45.

The free end of the intermediate member 1 is shaped as a large opening in which a correspondingly shaped air pump 2 may be arranged. The end of the air pump is formed with a constriction 49 which may be a press fit in one end of the intermediate member. The inner end face of the air pump has a pressure relief valve 50 which prevents the length of hose from being inflated too hard. Further, there is a hose connection 51 for connecting the pump with the rest of the apparatus by a hose 52. The intermediate member is constructed such that the hose may be stored in its coiled state in the cavity thereof when the apparatus is not in use. An inlet valve 28 is provided at the outer end of the air pump, and this valve can also serve as a vent valve when the air is to be released from the apparatus after completed use.

Figures 16, 17:
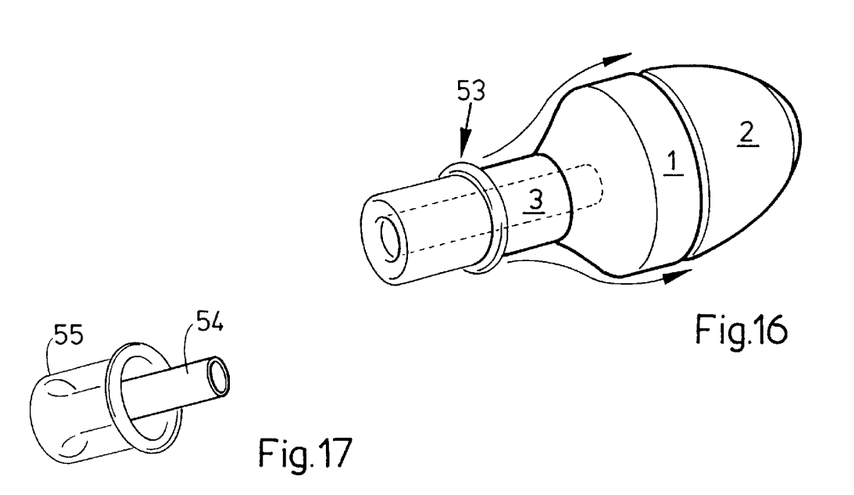
FIG. 16 shows a perspective view of the apparatus with partially applied cover.
FIG. 17 shows a perspective view of the partially applied cover.

FIGS. 14–17 of the drawing show an embodiment of the cover 53 intended for application on the mandrel 3 of the apparatus. The cover comprises a pipe 54 which is relatively stiff and which can be passed into the vent channel 15 of the apparatus. The pipe has a length such that it extends in the entire or substantially the entire length of the inner pipe, as indicated in FIG. 16. At one end the pipe merges into the cover part 55 itself, which is in a coiled state. The cover is applied by passing the pipe 54 into the vent channel of the apparatus until the coiled cover part 55 meets the end of the apparatus. The cover part 55 is then rolled inwardly over the mandrel and upwardly over the intermediate member 1 and extends across the opening with a terminating elastic ring. The cover is rolled off and discarded after completed use of the apparatus.

This embodiment of the apparatus is very convenient for the user as the air pump can readily be separated from the apparatus and be held in a convenient position, while the cover adds to the hygiene of the apparatus.

What is claimed is:

1. An apparatus, in particular for use in the antenatal period of pregnant women, the main function of said apparatus being to dilate muscular, tendinous and connective tissue in the pelvic floor so as to make these tissue structures more elastic, comprising (1) a mandrel for insertion into a vagina, said mandrel including a channel, a vent channel extending longitudinally therethrough which communicates externally of a user of the apparatus, and an elevated locking ring, and (2) length of hose which is mounted on said mandrel and is expandable by fluid passing through said channel in said mandrel, said elevated locking ring attaching said hose to said mandrel.

2. An apparatus according to claim 1, wherein an end of the mandrel has a slightly curved shape adapted anatomically to the vagina.

3. An apparatus according to claim 1, wherein a part of an apparatus adjoining the mandrel is formed with a curvature opposite the curvature of the mandrel.

4. An apparatus according to claim 3, wherein the vent channel has a rectilinear or substantially rectilinear course.

5. An apparatus according to claim 1, wherein the mandrel is formed with recesses so that it presents ribs in the area below a length of hose.

6. An apparatus according to claim 1, wherein the locking ring is provided with axially extending grooves on an outer side.

7. An apparatus according to claim 1, characterized in that it comprises a casing which may be pushed inwardly over the front end of the mandrel to cover a front portion of the length of hose (4) so that just the inner part of said length is active.

8. An apparatus according to claim 1, characterized in that the part (1) adjoining the mandrel has the shape of a bowl, and that the opening thereof and one end of the air pump (6) are constructed for detachable attachment of the air pump in the opening.

9. An apparatus according to claim 8, wherein the air pump is connected by a hose with the rest of the apparatus, and the bowl-shaped part is shaped such that the hose may be stored in it.

10. An apparatus according to claim 9, wherein the mandrel is formed by an outer pipe which, with an inner pipe, may be secured to the bowl-shaped part by threads.

11. An apparatus according to claim 12, wherein the length of hose is secured between one end of the inner pipe and the end of the part and between its other end and a collar on the inner pipe, respectively.

12. A protective cover for the apparatus according to claim 1, comprising a length of hose intended for application to the mandrel and at least secured at or near one end.

13. A protective cover according to claim 12, wherein the length of hose is provided with an elastic ring, one end being intended for application to the part of the apparatus which is present externally of a user the other end of the length of hose being intended for insertion into the vent channel.

14. A protective cover according to claim 12, wherein the one of the length of hose is shaped as a pipe intended for insertion into the vent channel of the apparatus.

15. A protective cover according to claim 12, wherein said protective cover is constructed so as to assume a maximum size in a transverse direction to restrict maximum expansion of the apparatus.

* * * * *